United States Patent
Woodroof et al.

(10) Patent No.: US 7,815,931 B2
(45) Date of Patent: Oct. 19, 2010

(54) ARTIFICIAL SKIN SUBSTITUTE

(76) Inventors: Ernest Aubrey Woodroof, 5930 Sea Lion Pl., Suite 100, Carlsbad, CA (US) 92010; Mitchell K. Enright, 5930 Sea Lion Pl., Suite 100, Carlsbad, CA (US) 92010

( * ) Notice: Subject to any disclaimer, the term of this patent is extended or adjusted under 35 U.S.C. 154(b) by 0 days.

(21) Appl. No.: 12/326,373

(22) Filed: Dec. 2, 2008

(65) Prior Publication Data
US 2009/0232878 A1  Sep. 17, 2009

Related U.S. Application Data

(63) Continuation-in-part of application No. 12/049,321, filed on Mar. 15, 2008, now abandoned.

(51) Int. Cl.
*A61F 13/00* (2006.01)
(52) U.S. Cl. .............. 424/447; 424/443; 623/15.12
(58) Field of Classification Search .......... 424/443, 424/447, DIG. 13; 156/77, 87; 264/319; 623/15.12

See application file for complete search history.

(56) References Cited

U.S. PATENT DOCUMENTS
4,725,279 A * 2/1988 Woodroof ............... 623/15.12

* cited by examiner

*Primary Examiner*—Christina Johnson
*Assistant Examiner*—Galen Hauth
(74) *Attorney, Agent, or Firm*—Steven W. Webb

(57) ABSTRACT

An improved skin substitute is presented comprised of non-biological materials produced with a series of regularly-spaced pores and a nylon weave netting. The top component is a thin (approximately 0.001" thick) silicone elastomer in which pore holes have been vacuum-pulled; physically attached to the silicone elastomer is a fine knitted nylon fabric (12/1, 15/1 denier); incorporated into the silicone/nylon structure are collagen peptides [about 10 micrograms per square centimeter of Porcine type 1—"the active component"] without cross-linking agent to enable a quick interaction with fibrin in the wound to achieve acute adherence. The vacuum-pulled holes provide a range of porosities to ensure minimum fluid accumulation beneath the skin substitute without wound desiccation. The range of hole diameters preferred in the present invention is 0.75 mm to 1.05 mm and at holes centered at ¼"-⅓". Providing a structure that has better acute adherence and minimal fluid accumulation beneath the Temporary Skin Substitute, which will reduce infection complications and maximize wound healing. Larger pieces of this skin substitute can be made to cover larger wounds, unlike previous skin substitutes.

1 Claim, 4 Drawing Sheets

Table 1. Characteristics of AWBAT vs Biobrane using Vacuum Technology

|  | Biobrane | AWBAT - S | AWBAT - D | AWBAT - M |
|---|---|---|---|---|
| Holes per sq. inch | 4 | 16 | 16 | 16 |
| Diameter of hole (inches) | .0615 | .0678 | .09645 | .09418 |
| & STDEV | .00707 | .00219 | .00298 | .00474 |
| Area of one hole | .00297 si. | .0036 si. | .0073 si. | .00696 si. |
| Percent Porosity | 1.2% | 6.00% | 12% | 11% |

Note the differences in standard deviation

AWBAT - S is 6 times more porous than Biobrane;
AWBAT (D or M) is 11 times more porous than Biobrane.
AWBAT - S contains holes 18.2% larger than Biobrane and has 4 times as many holes;
AWBAT (D or M) contains holes 86% larger than Biobrane and has 4 times as many holes.

Fig. 4

ARTIFICIAL SKIN SUBSTITUTE

RELATED APPLICATIONS

This application is a Continuation-in-Part of application Ser. No. 12/049,321 filed Mar. 15, 2008, now abandoned.

FIELD OF THE INVENTION

This invention relates to the field of artificial skin substitutes used for wound and burn dressings, and other purposes.

BACKGROUND OF THE INVENTION

A number of skin substitutes exist in the current market that address the wound dressing and burn dressing problem. There is currently no perfect product and there are still gaps in the capabilities of state-of-the-art artificial skin substitutes.

The present invention provides a precision, porous, stretchable membrane that fosters an ideal environment for the protection of existing cells and growth of new skin cells. The present invention promotes rapid adhesion to the wound as well as large sheet coverage (up to 24" by 24"), not offered by the state-of-the-art.

The present invention is made stretchable and tear resistant by using a fine knit nylon fabric. Additionally, the porosity of the overlying membrane is greater in terms of placement and area of pores, compared to the state-of-the-art. The membrane is semi-permeable, allowing water vapor transmission and preventing fluid accumulation in the wound.

As a consequence, the porosity of the membrane enhances the healing process, making it faster and safer. The membrane is also made capable of holding a biological agent that further increases the healing abilities of the covered area. These agents include biological agents such as chondrotin 6 sulfate, and others.

The present invention is easy to handle, flexible and stretchable, can be stored at room temperature, and is safe and sterile. Packaging and sterilizing of the invention is crucial. From a production and laboratory standpoint, manufacturing the invention is efficient in terms of time and materials. After manufacture, the product will be ready for immediate sterilization and shipping for use on patients.

TECHNICAL BACKGROUND

Some ideal properties of a skin substitute from (Rusczak, 2006) and Properties from (Robert H. Demling)

a. Rapid and sustained adherence to wound surface and Inner surface structure that permits cell migration, proliferation and in growth of new tissue (The most important criterion is adherence)

b. Absence of antigenicity c. Tissue compatible (Robert H. Demling)

d. Absence of local or systemic toxicity e. Impermeable to exogenous microorganisms f. Water vapor transmission similar to normal skin g. Rapid and sustained adherence to wound surface h. Conformal to surface irregularities i. Elastic to permit motion of underlying tissue j. Resistant to linear and shear stresses k. Tensile strength to resist fragmentation (when removed)

l. Inhibition of wound surface flora and bacteria m. Long shelf life, minimal storage requirements n. Low cost o. Minimize nursing care of wound p. Minimize patient discomfort q. Translucent properties to allow direct observation of healing r. Reduce heal-time s. Patient acceptance

PRIOR ART

Tissue Based Skin Substitutes

Alloderm by LifeCell, Inc—AlloDerm is human tissue and is processed from donated human skin. The tissue goes through a cell removal process while retaining the important biochemical and structural components. AlloDerm is, thus, acellular human tissue. U.S. Pat. No. 6,933,326—Particulate acellular tissue matrix Apligraf by Organogenesis Inc.—Apligraf is supplied as a living, bi-layered skin substitute: the epidermal layer is formed by human keratinocytes and has a well-differentiated stratum corneum; the dermal layer is composed of human fibroblasts in a bovine Type I collagen lattice. U.S. Pat. Nos. 4,485,096 5,106,949 5,536,656

Dermagraft by Smith & Nephew Inc—Dermagraft is a cryopreserved human fibroblast-derived dermal substitute; it is composed of fibroblasts, extracellular matrix, and a bioabsorbable scaffold. U.S. Pat. No. 4,963,489: Three-dimensional cell and tissue culture system Epicel by GenzymeBiosurgery—Epicel grafts are sheets of skin cells ranging from 2 to 8 cell layers thick. The grafts are grown or cultured from a postage stamp sized sample of patient's own healthy skin, which is sent to GenzymeBiosurgery for processing. The cells within the epidermis of the skin sample are separated and grown by a process called "tissue culture", which involves feeding the cells with specific nutrients and maintaining strict climate controls so that the cells multiply to form sheets of skin. During this process, irradiated mouse cells, also referred to as 3T3 cells, are used to promote cell growth and to ensure that there will be a sufficient number of grafts available as soon as possible for treatment. U.S. Pat. No. 6,964,869: Method and composition for skin grafts.

EZ Derm by Brennen Medical, Inc—A modified pigskin impregnated with a soluble silver compound intended for treatment of burns. Originally developed by Genetic Laboratories. US Patent Numbers: Stabilized silver-ion amine complex compositions and methods U.S. Pat. No. 6,923,990. This is not a patent for EZ Derm but it is related to the silver that EZ-Derm uses OrCel by Ortec International Inc.—A bilayered cellular matrix in which normal human allogeneic skin cells (epidermal keratinocytes and dermal fibroblasts) are cultured in two separate layers into a Type I bovine collagen sponge. Donor dermal fibroblasts are cultured on and within the porous sponge side of the collagen matrix while keratinocytes, from the same donor, are cultured on the coated, non-porous side of the collagen matrix.

TransCyte by Smith and Nephew, Inc—Consists of a polymer membrane and newborn human fibroblast cells cultured under aseptic conditions in vitro on a nylon weave. Prior to cell growth, this nylon weave is coated with porcine dermal collagen and bonded to a polymer membrane (silicone). This membrane provides a transparent synthetic epidermis when the product is applied to the burn.

As fibroblasts proliferate within the nylon weave during the manufacturing process, they secrete human dermal collagen, matrix proteins and growth factors. Following freezing, no cellular metabolic activity remains; however, the tissue matrix and bound growth factors are left intact. The human fibroblast-derived temporary skin substitute provides a temporary protective barrier. TransCyte is transparent and allows direct visual monitoring of the wound bed.

Silver Based Skin Substitutes

Aquacell Ag

Silver Powered Antimicrobial Dressing

ActiCoat

Using Unique Silver Technology:

SILCRYST Nanocrystalline

Other Synthetic/Similar to our Membrane Skin Substitutes

Biobrane, Biobrane-L by Bertek Pharmaceuticals—Biobrane Æ is a biocomposite temporary wound dressing constructed of an ultrathin, semipermeable silicone film with a nylon fabric partially imbedded into the film. The fabric presents to the wound bed a complex 3-D structure of trifilament thread to which porcine dermal collagen has been chemically bound. Blood/sera clot in the nylon matrix, thereby firmly adhering the dressing to the wound until epithelialization occurs. U.S. Pat. No. 4,725,279.

Integra Bilayer Matrix Wound Dressing by Integra LifeSciences Corp.—an advanced wound care device comprised of a porous matrix of cross-linked bovine tendon collagen and glycosaminoglycan and a semi-permeable polysiloxane (silicone) layer.

Laserskin by Fidia Advanced Biopolymers—Lam, P. K. et al; "Development and evaluation of a new composite Laserskin graft", J of Trauma: Injury, Infection and Critical Care. 47, 1999. pp. 918-922.

Oasis Wound Matrix by Healthpoint—A biologically derived extracellular matrix-based wound product that is compatible with human tissue. Unlike other collagen-based wound care materials, OASIS is unique because it is a complex scaffold that provides an optimal environment for a favorable host tissue response, a response characterized by restoration of tissue structure and function.

Glucan II—A smooth gas permeable polymeric layer attached to the mesh matrix. A highly advanced carbohydrate dressing with Beta-Glucan.

SUMMARY OF THE INVENTION

The present invention produces thin silicon/nylon membranes on flat Teflon surfaces. In its first instantiation, either a laser piercing or a unique needle piercing was used to produce pores in the membrane. Both methods have been abandoned, and the present invention uses a new method that creates no damage to the nylon weave component of the membrane.

The present silicone/nylon membrane has been developed for applications on wounds or burns. These applications include, but are not limited to superficial wounds, donor sites, meshed autograph sites, and specialized wound locations such as the hands.

Silicone Technology—The present invention uses a Silicone Dispersion mixed with a 15% Solution of Xylene: Heat Cured Mfg. Part Number V40000-SP. It is a custom mixed product for this use and specifically requested for this application. The supplier is Factor II.

Knitting Technology—The present invention uses a knitting machine with a 13 inch cylinder with 1152 needles. It can knit varying length of tubes.

The boarding process follows the knitting of the tube and controls the final width (and length) of the nylon. The form size used in the boarding process is important. The current form is 15¾ inches wide by 32 inches long. The top of the form is tapered for approximately 2 inches. The boarding chamber is larger and can accommodate a form up to 19 inches wide and 32 inches long. There is a significant advantage over competing technologies with a larger final knitted product, allowing for larger final silicone/nylon membranes.

Fabric can be knitted in custom weaves. The preferred weaves and settings for the machine are detailed in a series of technical guides. The different weaves give the final product varying characteristics and are critical in producing the proper end result.

Plate Technology—A process to cure a precision membrane after combining it with nylon on a flat Teflon coated, drilled plate has been developed and is included below. The plate used to cure the membrane is formed out of a rigid metal in a honey-comb structure with a low density. The low density of the plate gives it low heat sinking properties. The structure allows for a very strong and rigid design, while remaining extremely flat. It is absolutely critical that the surface is as flat as possible so as to allow for the silicone dispersion to be layered consistently, flat, and level, with no variations in thickness.

The plate is coated with a low adhesion Teflon™ coat (Silverstone™). The coating is critical as the membrane will not release properly without it. Three substances were tested before deciding on a final product, including White virgin Teflon™ and a standard Teflon™ coating. The plates are cleaned between uses so that no residue is left behind on the final silicone/nylon membrane.

Several hole making technologies have been used successfully to produce the silicone membrane. The following are the technologies available and used in this invention.

Piercing Technology—A needle guide and puncture plate system has been used with needles of various sizes interchangeable in the system. The puncture plate is composed of two metal plates with drilled holes. A membrane is placed between the two plates, and then using a needle holder with needles in it, the needles are lined up with holes in the puncture plate and are pressed through the membrane. To increase the effectiveness of the needle puncture system, a heat plate can be used to warm the needles, creating a cleaner puncture in the membrane.

The process is as follows: cured raw material is mounted on parchment paper and cut to size, a cut sheet is mounted between the upper and lower puncture plates, needle guides are inserted through the puncture plate guide holes and through the product, the needle guides are removed from plates, and product is removed from plates. Finish cut and package.

The downside to this system was that puncturing holes is time consuming and labor intensive. The process cannot be done in one step and it generates debris. There is limited control of hole geometry. Damage is done to the nylon fabric, which reduces the strength and stretchability of the nylon.

Porthole/Vacuum Technology—The preferred embodiment method for making pore holes involves the use of a flat Teflon™ coated plate with drilled holes in combination with a vacuum box to create pores quickly during the layering process. This method allows removal of the silicone to make the pore holes in a manner that does not disturb the three-dimensional structure of the knitted nylon.

The Teflon plate is as described in the Teflon Plate Technology section, with one addition: it has been "drilled", meaning holes/voids have been put into the plate with a proprietary hole making method. The holes can be put into the plate in a number of ways, including top drilling, back drilling, back pre-drilling with final drilling/cleaning. The holes can be formed in a cylinder shape, or in a "volcano" shape. Each method has various advantages. Holes can be drilled in a random or symmetrical pattern. Holes can be created in various sizes throughout the plate. A common technique would be to have an even pattern of "volcano" holes, with every fourth hole being a larger size.

The modified Teflon™ plate is placed over a vacuum system. The vacuum system consists of a box the size of the above Teflon plate. The box is sized such that when the plate is placed on top of it, an airtight seal is created. The side of the box has an opening where a vacuum or airflow system can be attached.

At this point, silicone is quickly layered over the Teflon plate. A vacuum is then created within the box, drawing air from above the Teflon plate, into the box, and then to the vacuum device. The vacuum is created by "popping" the vacuum box, meaning the vacuum is applied only for a moment. This "popping" method is critical as it removes silicone from the top of the plate where holes are located. It does this without dragging excess silicone into the plate or disturbing the knitted nylon's structure.

The overall process is as follows: Silicone is applied to distribution sheet. Excess silicone in a customized pattern is removed via the vacuum system. Nylon fabric is applied without wrinkles to the silicone dispersion. Finally, the plate with the nylon and silicone layer is allowed to cure before removal of the porous silicone/nylon membrane.

Results: Over previous technology, the Porthole Technology drastically reduces production time. It generates no debris. Allows for perfect control of hole geometry and porosity. It creates no damage to nylon fabric and allows for greater flexibility in customizing hole/void patterns.

Table 1 shows the comparison in hole placement between the invention (AWBAT) and the leading skin substitute, Biobrane.

Biological/Active Component of the Skin Substitute

Additives—A silicone/nylon based membrane will adhere to a wound and protect it from the environment. The ideal environment it creates for the wound can be amplified through the addition of biological agents.

One biological additive provided by this invention is a mobile form of gelatin. Gelatin 300 Bloom Pork 30 Mesh USP/NF, Mfg./Supplier Part Number PS-300-030-N-G. In this application, the terms Gelatin, Collagen, and Collagen Peptide may be used interchangeably.

The gelatin is mixed with water (or other solution) and is "painted" onto the cured silicone/nylon. It is then allowed to dry. The amount of gelatin applied is controlled at 10 micro grams per square centimeter through the rate and volume of spray.

This is the preferred embodiment of the invention. The technology to create the pore holes by means of the vacuum popping box is listed as the preferred embodiment of this invention, and other methods are possible and are within the contemplation of this patent.

DETAILED SPECIFICATION

Figure 1:
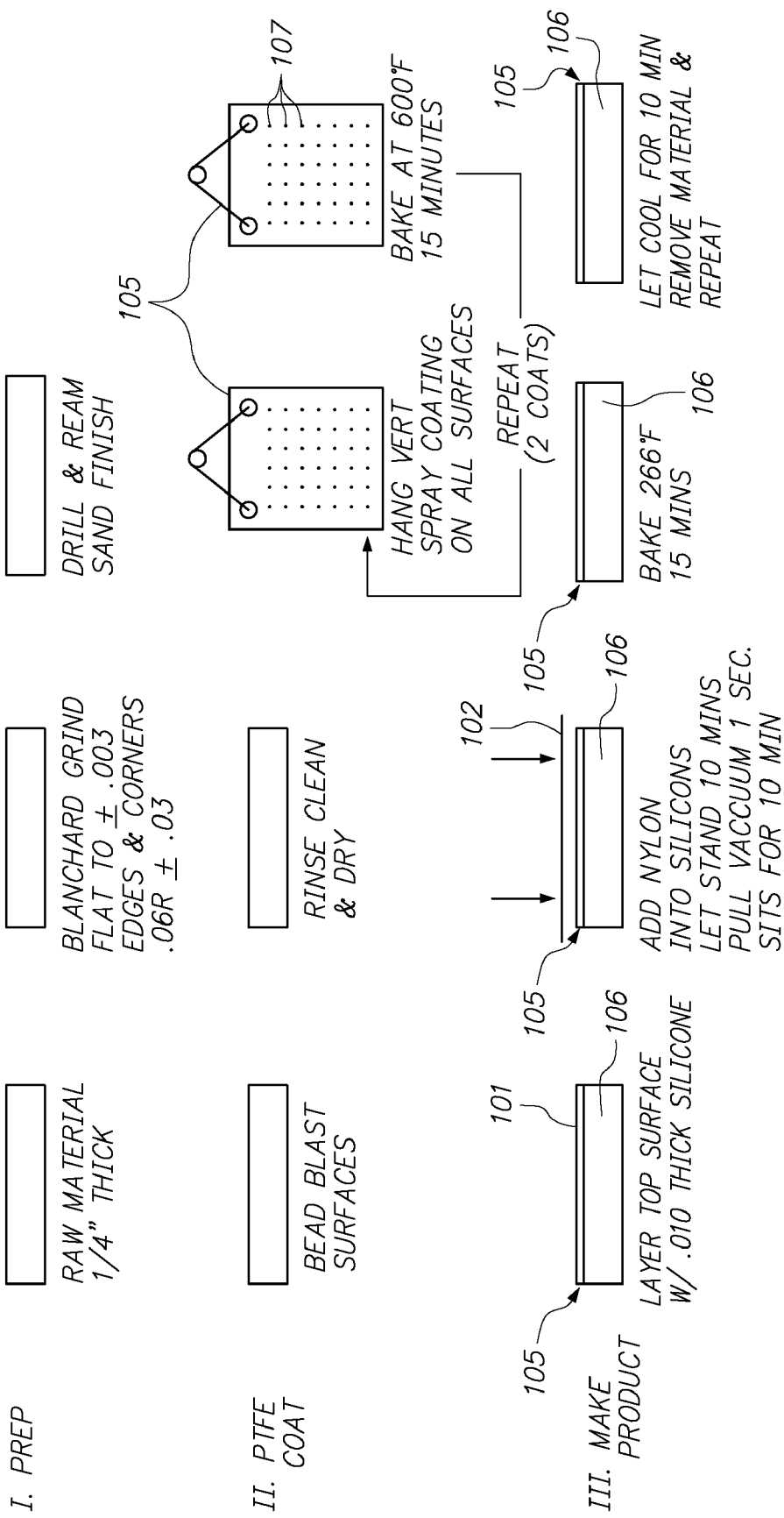
FIG. 1. Perspective view of the invention
FIG. 2. Needle Block Drawing
FIG. 3. Silicone Layering Tool Drawing
FIG. 4. Table 1
Figure 2:
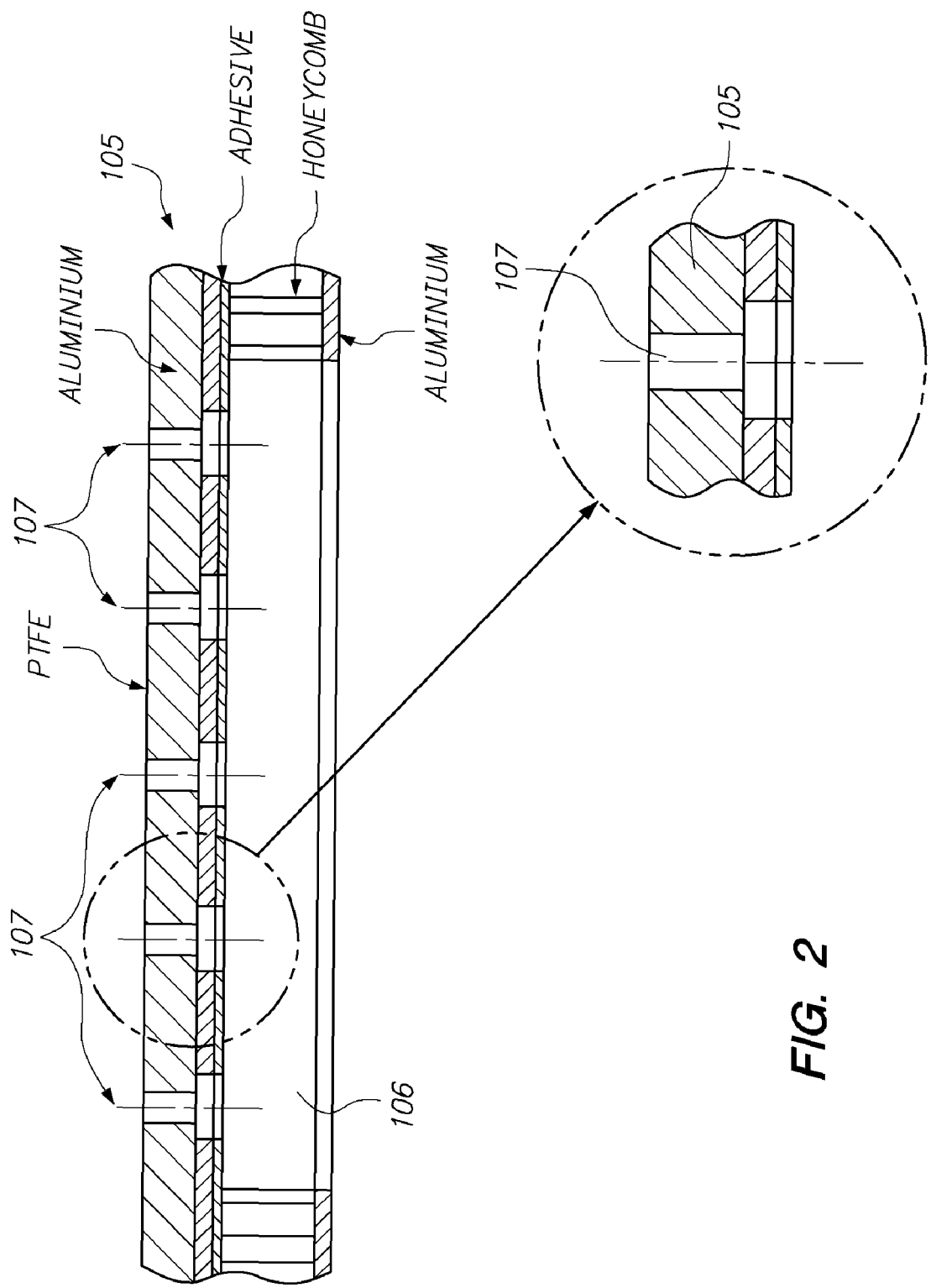
Figure 3:
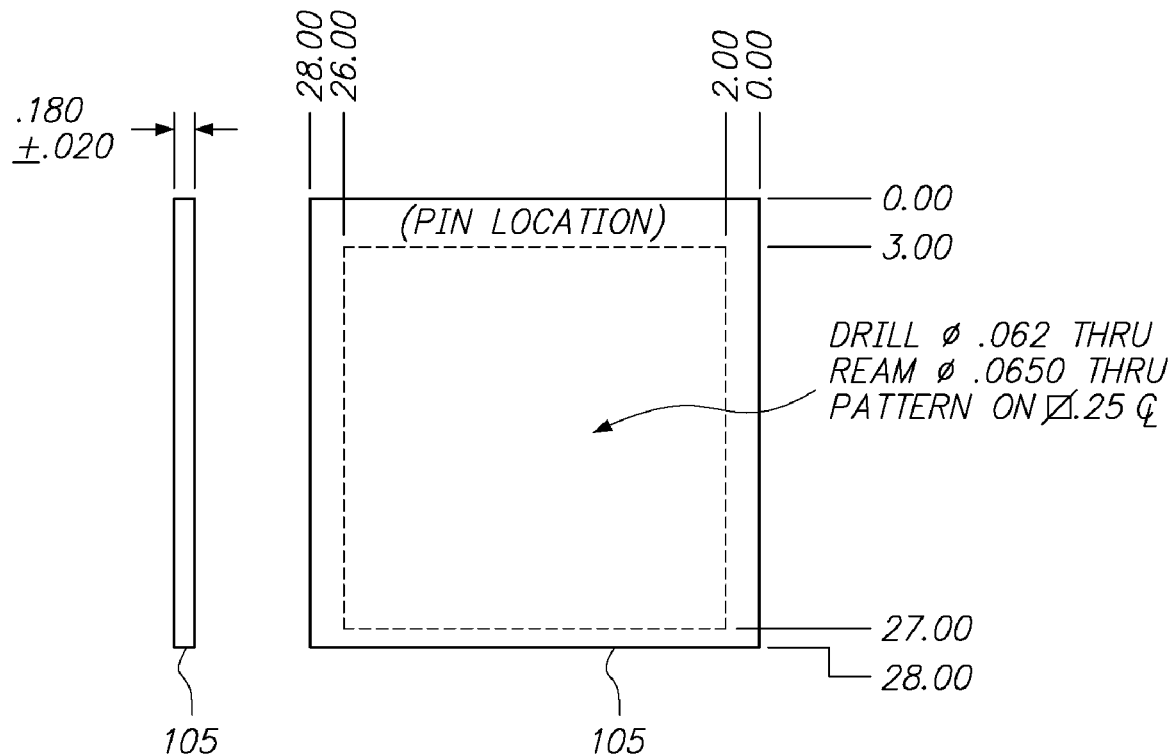

The invention 100 is comprised of two layers of material, a membrane layer 101 and a nylon weave 102, as shown in FIG. 1. The membrane layer 101 is fixedly attached to the nylon weave 102 during manufacture. The two layers of the invention are made from non-organic material used as a skin substitute.

The membrane layer 101 possesses a plurality of pores 103 arranged across its surface in a regular pattern. The pores 103 are produced in its surface during manufacture by one of several means, including penetration of the membrane by needles, by laser beam, and by means of vacuum suction. The preferred mode is by means of vacuum suction.

The nylon weave 102 is a produced by a knitting machine with a 13 inch cylinder with 1152 needles. It can knit varying length of tubes of the nylon weave 102.

The boarding process follows the knitting of the tube and controls the final width (and length) of the nylon. The current form is 15¾ inches wide by 32 inches long. The top of the form is tapered for approximately 2 inches. The boarding chamber is larger and can accommodate a form up to 19 inches wide and 32 inches long.

The nylon weave 102 can be knitted in custom weaves. The preferred weaves and settings for the machine are detailed in an industry standard specification sheet. The different weaves give the invention 100 varying characteristics and are critical in producing the proper end result.

The preferred process to produce the invention 100 is to cure the membrane layer 101 after combining it with nylon weave 102 on a flat Teflon™ coated, drilled plate 105. The plate 105 used to cure the membrane layer 101 is formed out of an aluminum honey-comb structure with a low density. The low density of the plate 105 gives it low heat sinking properties. The honey-comb like structure allows for a very strong and rigid design, while remaining extremely flat. It is critical that the surface is flat in order to allow the silicone dispersion 101 to be layered consistently, flat, and level, with no variations in thickness.

The plate 105 is coated with a low adhesion Teflon™ coat (Silverstone™). The coating is critical as the invention will not release properly without it. Three substances were tested before selecting the final plate composition including White virgin Teflon™ and a standard Teflon™ coating. The plates are cleaned between uses and no residue is left behind on the final silicone/nylon membrane.

To implement the needle piercing method of pore production, a needle guide and puncture plate system is used. Needles of various sizes can be used and interchanged in the system. The puncture plate is composed of two metal plates, one with drilled holes. The invention 100 is placed between the two plates, and then using a needle holder with needles in it, the needles are lined up with holes in the puncture plate and are pressed through the invention 100. To increase the effectiveness of the needle puncture system, a heat plate can be used to warm the needles, creating a cleaner puncture in the invention.

The process is as follows: cured raw material is mounted on parchment paper and cut to size, a cut sheet is mounted between the upper and lower puncture plates, needle guides are inserted through the puncture plate guide holes and through the invention 100, the needle guides are removed from the plates, and the invention is removed from plates.

The preferred embodiment method for making pores 103 involves the utilization of a flat porous Teflon™ plate in combination with a vacuum box 106 to create the pores 103 quickly, following combining the nylon weave 102 with the silicone dispersion 101.

At this point, a silicone dispersion is quickly layered over the Teflon coated plate 105. A vacuum is then created within the box 106, drawing air from above the Teflon plate 105, into the box 106, and then to the vacuum device. The vacuum is created by "popping" the vacuum box 106, meaning the vacuum is applied only for a moment. This "popping" method is critical as it removes the silicone dispersion from the top of the plate 105 where the plurality of holes 107 are located. It does this without dragging excess silicone into the plate 105 or changing, altering, or modifying the three-dimensional structure of the nylon component.

The overall process is as follows: Silicone dispersion is applied to make the membrane layer 101. Excess silicone in customized pattern is removed via the vacuum system 110. nylon weave 102 is applied wrinkle free to the membrane layer 101. Finally, the plate with membrane layer 101 and nylon weave 102 is allowed to cure before removal.

As an alternative to introducing holes into the silicone/nylon membrane, there is a process of creating voids. The technology to create these voids as listed is the preferred embodiment of this invention.

Methods of Production of the Invention By Creating Voids
Preparation

All operations done in clean room.

Ensure that environment is clean and dust free.

Ensure that void making board is clean and free of debris.

Inspect holes for cleanliness and absence of debris.
Layering Process:

Layer top surface of board with 0.010 inch silicone

Add nylon weave to silicones

Let stand 10 minutes
Hole Making Process:

Pull vacuum for 1 second

Let stand for 10 minutes

Bake at 266 degrees F. for 15 minutes

Let cool for 10 minutes

Remove material

The apparatus and methods described are the preferred and alternate embodiments of this invention, but other methods are possible and are within the contemplation of this patent.

What is claimed is:

1. A skin substitute,
   the skin substitute comprised of two layers of material, a membrane layer and a nylon weave,
   the membrane layer fixedly attached to the nylon weave during manufacture of the skin substitute, the membrane layer and nylon weave made from non-organic material,
   the membrane layer possessing a plurality of pores arranged across its surface in a pattern,
   the pattern of pores selected from the group consisting of random and regular,
   the plurality of membrane layer pores manufactured in such a manner that the porosity of the membrane layer exceeds 16 pores per square inch and six percent of the membrane area,
   the improved porosity of said membrane layer to water vapor providing decreased fluid pressure on healing wounds and reduced incidences of infection,
   the nylon weave manufactured in a plurality of custom weaves, the different weaves making the skin substitute stretchable in two directions or stretchable in four directions, providing a dense weave or a loose weave,
   the membrane layer pores produced in said membrane by use of vacuum suction,
   the membrane layer and nylon weave impregnated at manufacture with a plurality of biological and non-biological substances, the biological substances comprising collagen, the collagen selected possessing no cross-linking agents,
   the collagen and other biological and non-biological substances positioned on the membrane and in the nylon weave for therapeutic purposes.

* * * * *